US009155903B2

(12) United States Patent
Brown et al.

(10) Patent No.: US 9,155,903 B2
(45) Date of Patent: *Oct. 13, 2015

(54) WEARABLE CARDIAC DEFIBRILLATOR RECEIVING INPUTS BY BEING DELIBERATELY TAPPED AND METHODS

(71) Applicant: West Affum Holdings Corp., Grand Cayman, KY (US)

(72) Inventors: David Thomas Brown, Lynnwood, WA (US); Gary Debardi, Kirkland, WA (US); David Peter Finch, Bothell, WA (US); Krystyna Szul, Seattle, WA (US)

(73) Assignee: West Affum Holdings Corp., Grand Cayman (KY)

( * ) Notice: Subject to any disclaimer, the term of this patent is extended or adjusted under 35 U.S.C. 154(b) by 123 days.

This patent is subject to a terminal disclaimer.

(21) Appl. No.: 14/014,987

(22) Filed: Aug. 30, 2013

(65) Prior Publication Data

US 2014/0085081 A1    Mar. 27, 2014

Related U.S. Application Data

(60) Provisional application No. 61/704,966, filed on Sep. 24, 2012.

(51) Int. Cl.
*G08B 1/08*    (2006.01)
*A61N 1/39*    (2006.01)
*A61N 1/04*    (2006.01)

(52) U.S. Cl.
CPC .............. *A61N 1/3993* (2013.01); *A61N 1/046* (2013.01)

(58) Field of Classification Search
None
See application file for complete search history.

(56) References Cited

U.S. PATENT DOCUMENTS

| 6,473,638 | B2 * | 10/2002 | Ferek-Petric ................. 600/523 |
| 7,974,689 | B2 | 7/2011 | Volpe et al. |
| 2008/0001735 | A1 * | 1/2008 | Tran ......................... 340/539.22 |
| 2009/0306525 | A1 * | 12/2009 | Pinter et al. ................... 600/500 |
| 2011/0022105 | A9 * | 1/2011 | Owen et al. ....................... 607/5 |
| 2013/0173299 | A1 | 7/2013 | Hyde et al. |
| 2013/0218252 | A1 * | 8/2013 | Kaib et al. ..................... 607/142 |
| 2013/0231711 | A1 * | 9/2013 | Kaib ................................ 607/5 |
| 2013/0253600 | A1 * | 9/2013 | Drew et al. ....................... 607/5 |
| 2014/0046391 | A1 * | 2/2014 | Cowan et al. ..................... 607/5 |
| 2014/0070957 | A1 * | 3/2014 | Longinotti-Buitoni et al. ......................... 340/870.01 |
| 2014/0088739 | A1 * | 3/2014 | Ellis et al. ....................... 700/91 |
| 2014/0104059 | A1 * | 4/2014 | Tran ......................... 340/539.12 |
| 2014/0296931 | A1 * | 10/2014 | Chapman et al. ................. 607/7 |
| 2014/0313051 | A1 * | 10/2014 | Fain et al. ................ 340/870.02 |
| 2014/0336519 | A1 * | 11/2014 | Kaib et al. ..................... 600/515 |

* cited by examiner

*Primary Examiner* — Julie Lieu
(74) *Attorney, Agent, or Firm* — Kavounas Patent Law Office, PLLC.

(57) ABSTRACT

A wearable defibrillation system includes an output device and a motion sensor. The output device emits a sound or a vibration for the patient, who responds by deliberately tapping the system. The motion sensor registers the tapping, and interprets it as a reply from the patient. The reply can be that the patient is conscious, or convey data that the patient enters by tapping the right number of times, or that the patient wants attention, and so on. Since the patient does not need direct access to the wearable defibrillation system for tapping it, he or she can wear it under their other garments, which helps preserve their dignity and privacy.

26 Claims, 11 Drawing Sheets

WEARABLE DEFIBRILLATOR SYSTEM

WEARABLE DEFIBRILLATOR SYSTEM

*COMPONENTS OF EXTERNAL DEFIBRILLATOR*

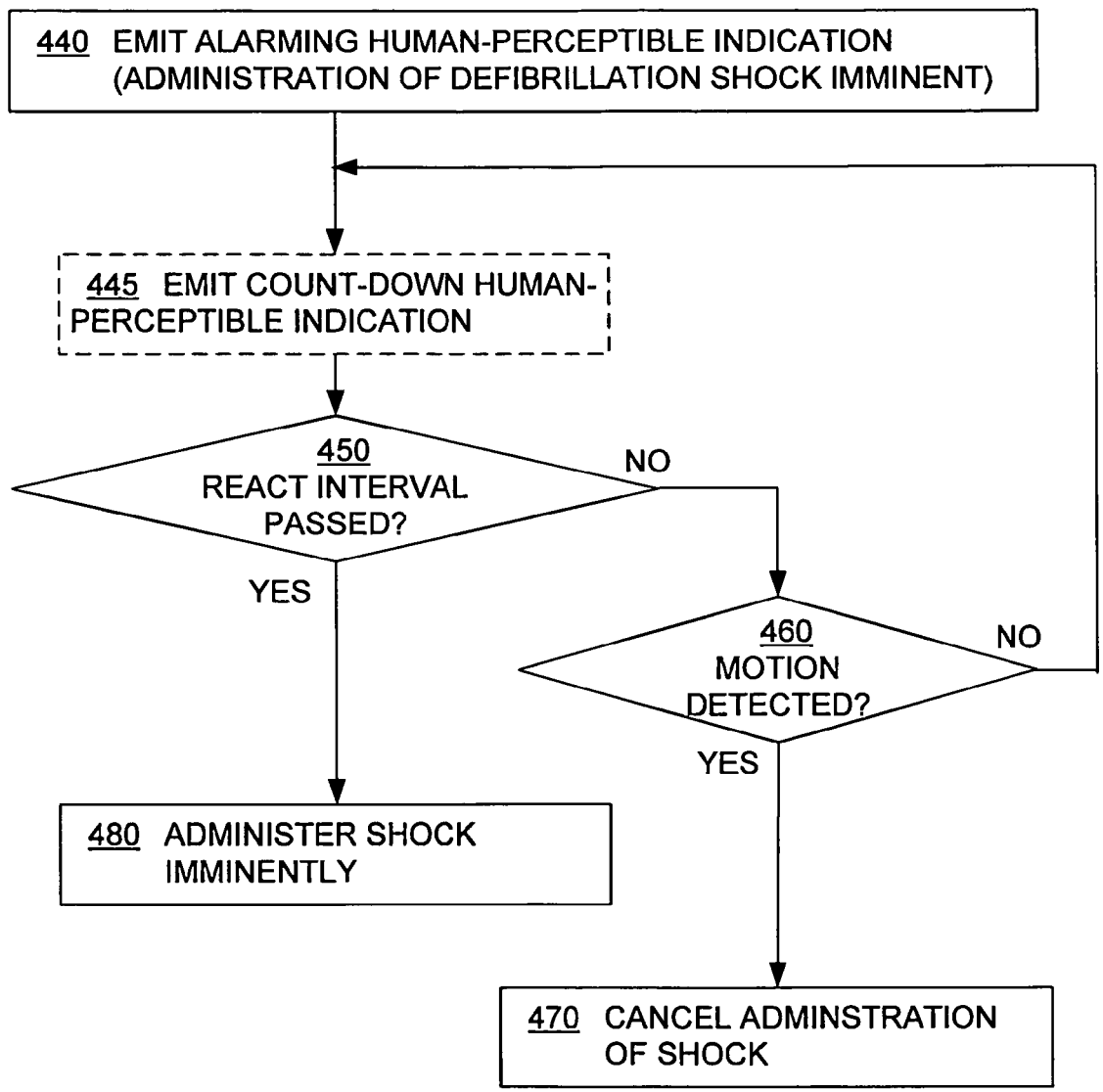

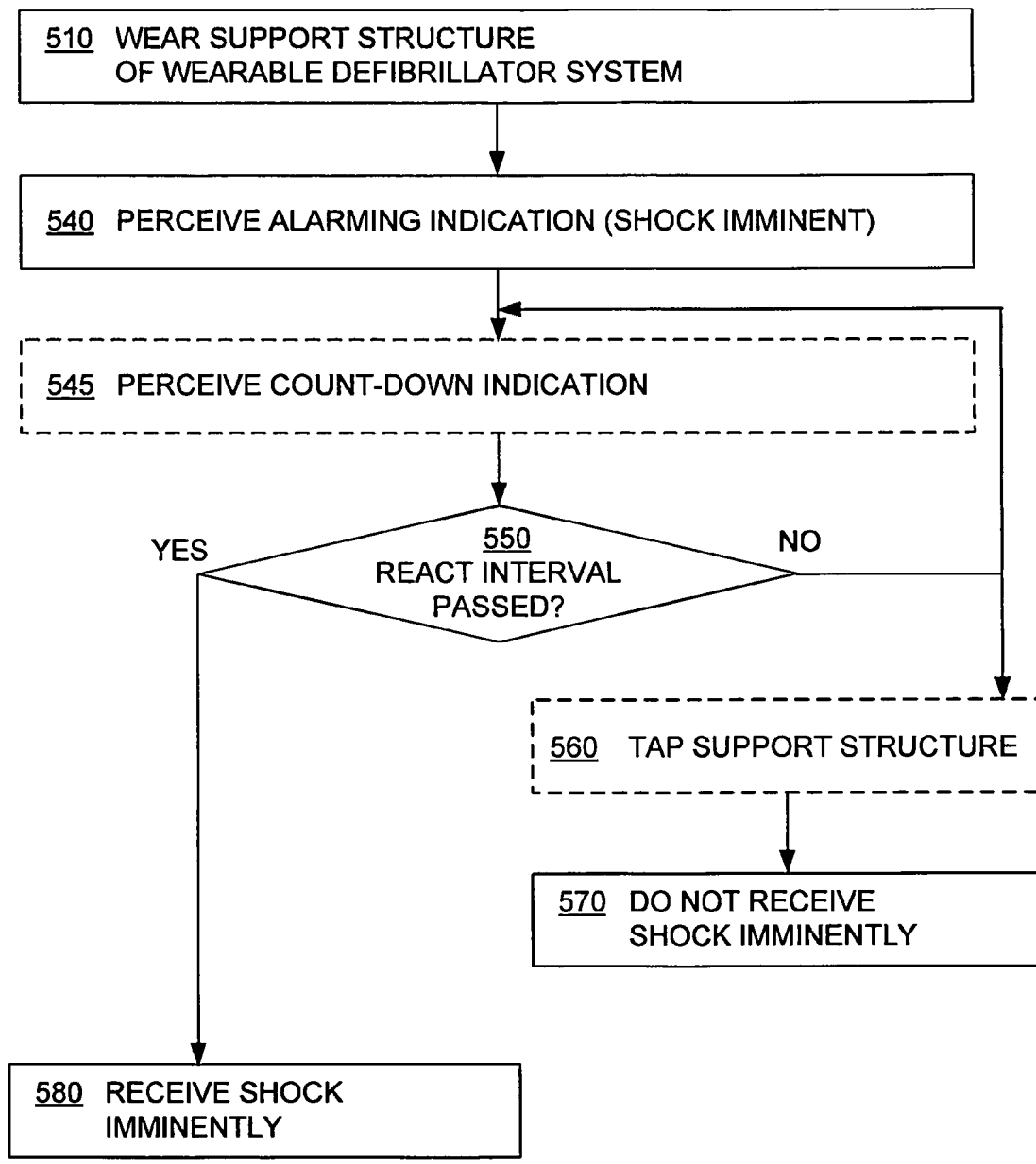
FIG. 5   *METHODS*

| Step | Device | | | Patient |
|---|---|---|---|---|
| | Voice | Vibration | Therapy | |
| 1 | | Active | | |
| 2 | "Shock Delivery Imminent. Tap to cancel shock" | | | |
| 3 | | | | Falls down, creates inadvertent tap |
| 4 | "Tap detected. Tap again to confirm shock cancellation" | | | |
| 5 | <Patient is unconscious. Five seconds elapse without a confirmation tap> | | | |
| 6 | "Stand Clear" | | | |
| 7 | | | Shock Delivered | |
| 8 | | | | Patient converted to NSR |

SAMPLE SEQUENCE OF EVENTS

FIG. 6A

| Step | Device | | | Patient |
|---|---|---|---|---|
| | Voice | Vibration | Therapy | |
| 1 | | Active (indicates therapy is imminent) | | |
| 2 | "Shock Delivery Imminent. Tap to cancel shock" | | | |
| 3 | | | | Tap #1 |
| 4 | "Tap detected. Tap again to confirm shock cancellation" | | | |
| 5 | | | | Tap #2 |
| 6 | "Shock cancelled" | | | |

SAMPLE SEQUENCE OF EVENTS

FIG. 6B

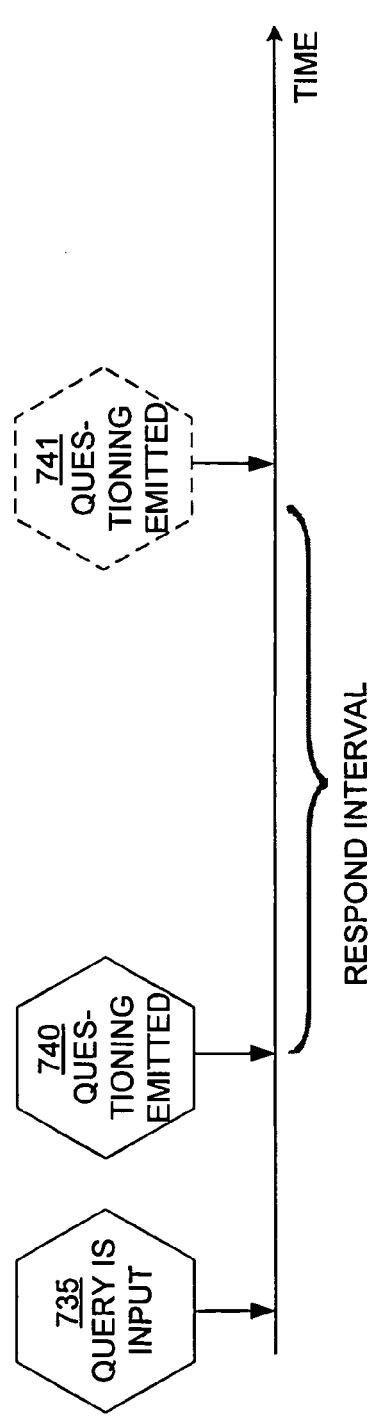
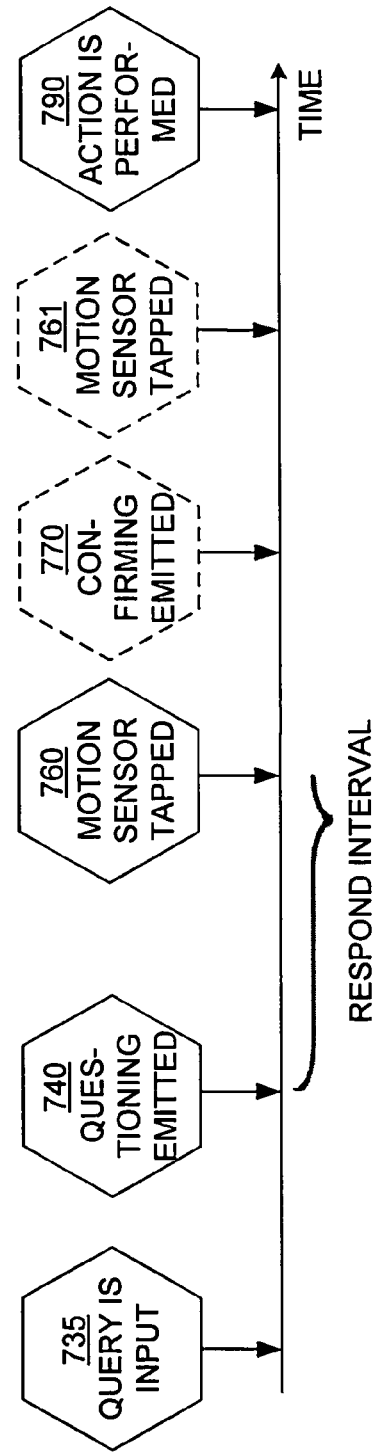

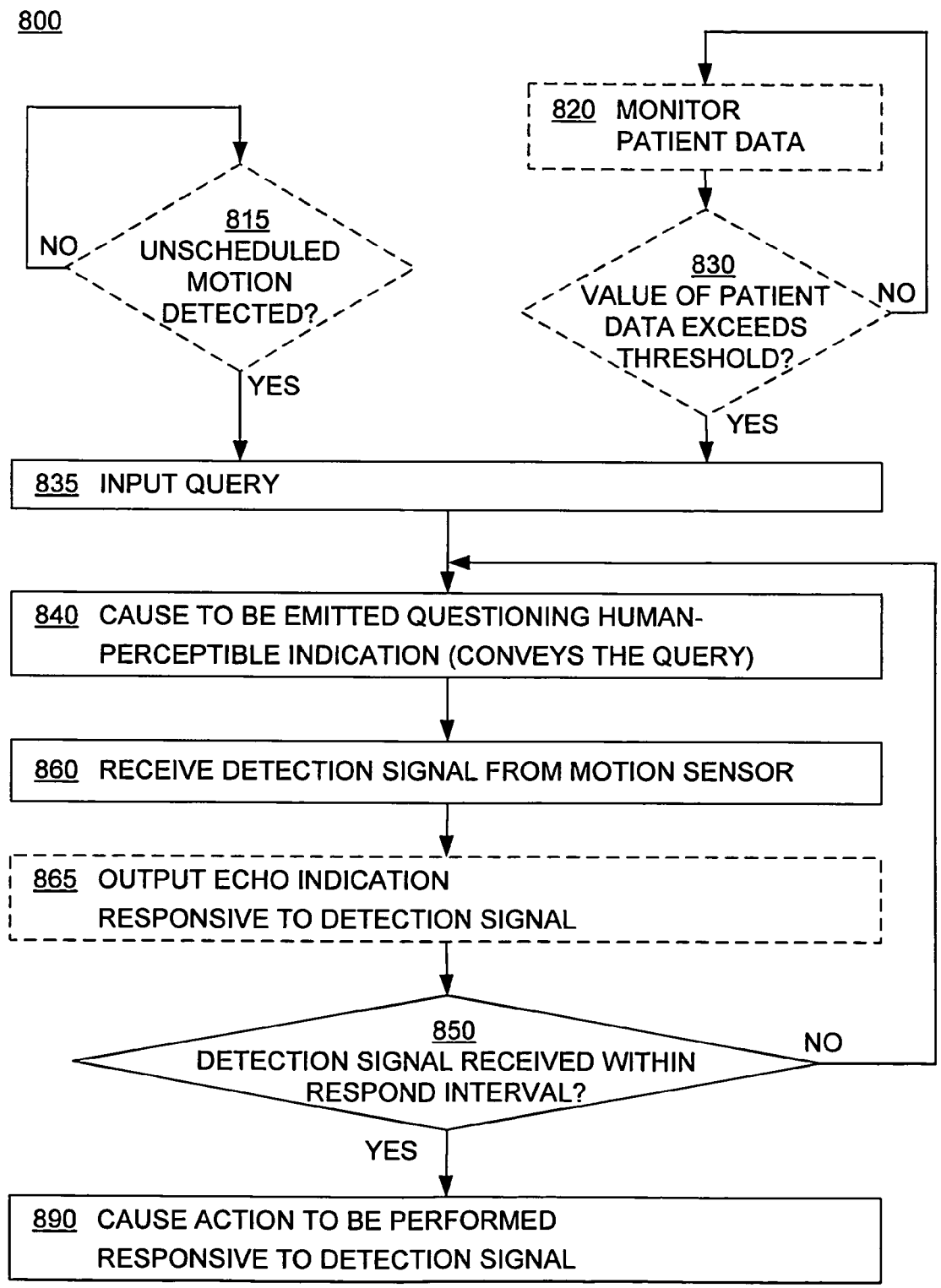
FIG. 8    METHODS

| Step | Device | | | Patient |
|---|---|---|---|---|
| | Voice | Vibration | Storage | |
| 1 | | | | Feels ill, wants to record event |
| 2 | | | | Tap #1 |
| 3 | "Tap detected. Tap again to confirm event" | | | |
| 4 | | | | Tap #2 |
| 5 | "Patient event recorded at 4:39 p.m." | | Save patient event | |

SAMPLE SEQUENCE OF EVENTS

FIG. 10

WEARABLE CARDIAC DEFIBRILLATOR RECEIVING INPUTS BY BEING DELIBERATELY TAPPED AND METHODS

CROSS REFERENCE TO RELATED PATENT APPLICATIONS

This patent application claims priority from U.S. Provisional Patent Application Ser. No. 61/704,966, filed on Sep. 24, 2012, titled: "WEARABLE MEDICAL DEVICE RESPONDING TO MECHANICAL TAPPING AS MEANS OF COMMUNICATION", the disclosure of which is hereby incorporated by reference for all purposes.

BACKGROUND

When people suffer from some types of heart arrhythmia, the result may be that blood flow to various parts of the body is reduced. Some arrhythmias may even result in a Sudden Cardiac Arrest (SCA). SCA leads to death very quickly, e.g. within 10 minutes, unless treated in the interim.

People who have had a heart attack have an increased risk of SCA, and therefore it is recommended that they receive an Implantable Cardioverter Defibrillator ("ICD"). An ICD has internal electrodes, and continuously monitors the person's electrocardiogram ("ECG"). If certain types of heart arrhythmia are detected, then the ICD delivers an electric shock through the heart.

People with increased risk of an SCA are sometimes given a wearable external defibrillator system. The recipients typically include those who have had a heart attack, or SCA, or are considered at risk, but have not yet had an ICD implanted. A wearable defibrillator system typically includes a harness, vest, or other garment for wearing by the patient. The system includes a defibrillator and external electrodes, which are attached on the inside of the harness, vest, or other garment. When the patient wears the system, the external electrodes may then make good electrical contact with the person's skin, and therefore can help monitor the patient's ECG. If a shockable heart arrhythmia is detected, then the defibrillator delivers the appropriate electric shock through the body, and thus through the heart.

BRIEF SUMMARY

The present description gives instances of wearable defibrillation systems, software, and methods, the use of which may help overcome problems and limitations of the prior art.

In one embodiment, a wearable defibrillation system includes an output device and a motion sensor. The output device emits a sound or a vibration for the patient, who responds by deliberately tapping the system. The motion sensor registers the tapping, and interprets it as a reply from the patient. The reply can be that the patient is conscious, or convey data that the patient enters by tapping the right number of times, or that the patient wants attention, and so on.

Advantages over the prior art arise from the fact that the motion needed by the patient for tapping is less exact than, say, finding and pushing buttons. In fact, such buttons need not be provided, saving in cost. And less dexterity is required from the patient, while tapping the system in a stressful situation. Moreover, since the patient does not need direct access to the wearable defibrillation system for tapping it, he or she can wear it under their other garments, which helps preserve their dignity and privacy. Embodiments can also help people who are hard of hearing, by having a query from the system encoded as a different pattern of vibrations, and so on.

These and other features and advantages of this description will become more readily apparent from the following Detailed Description, which proceeds with reference to the drawings, in which:

BRIEF DESCRIPTION OF THE DRAWINGS

FIG. 4 is a flowchart for illustrating methods according to embodiments.

FIG. 5 is a flowchart for illustrating methods according to embodiments.

FIG. 6A is a diagram showing a sample sequence of events according to embodiments.

FIG. 6B is a diagram showing a sample sequence of events according to embodiments.

FIGS. 7A and 7B are diagrams showing sample sequences of events according to additional embodiments.

FIG. 8 is a flowchart for illustrating methods according to additional embodiments.

FIG. 10 is a diagram showing a sample sequence of events according to additional embodiments.

DETAILED DESCRIPTION

As has been mentioned, the present description is about wearable defibrillation systems. Embodiments are now described in more detail.

Figure 1:
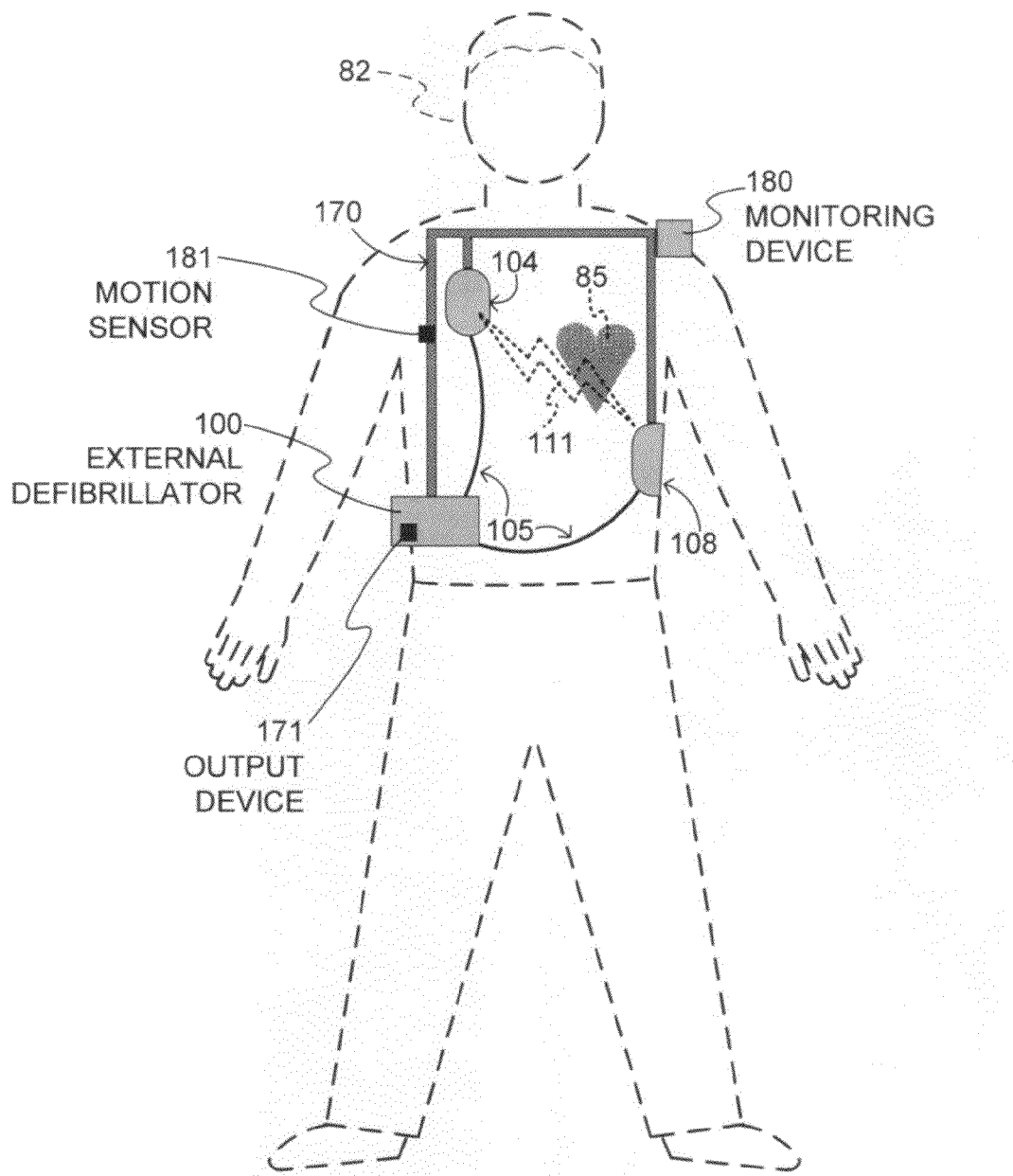
FIG. 1 is a diagram of components of a wearable defibrillator system, made according to embodiments.

FIG. 1 depicts components of a wearable defibrillator system, which is intended to be worn by a patient 82. Patient 82 may also be referred to as person 82, and wearer 82 since he or she wears components of the wearable defibrillator system.

One of the components of a wearable defibrillator system according to embodiments is a support structure, which is configured to be worn by patient 82. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

In FIG. 1, a generic support structure 170 is shown relative to the body of person 82, and thus also relative to his or her heart 85. Structure 170 could be a harness, a vest, one or more belts, a garment, as per the above; it could be implemented in a single component, or multiple components, and so on. Structure 170 is wearable by person 82, but the manner of wearing it is not depicted, as structure 170 is depicted only generically in FIG. 1.

A wearable defibrillator system is configured to defibrillate the person, by delivering electrical charge to the person's body in the form of an electric shock. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, all components of defibrillator 100 may be therefore coupled to support structure 170. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock, goes also through heart 85, in an attempt to restart it, for saving the life of person 82.

A prior art defibrillator typically decides whether to defibrillate or not based on an electrocardiogram ("ECG") of the patient. However, defibrillator 100 can defibrillate or not also based additionally on other inputs.

The wearable defibrillator system may also include an output device 171, for communicating with patient 82. Output device 171 may be a part of a user interface 270 that is described later with reference to FIG. 2.

In some embodiments, when the charge is intended to be delivered imminently by defibrillator 100 as electric pulse 111, output device 171 emits an alarming human-perceptible indication for patient 82 to notice. The emitting can be performed in a number of ways. For example, output device 171 may include a vibration mechanism, and the alarming human-perceptible indication includes an emitted vibration. For another example, output device 171 may include a speaker, and the alarming human-perceptible indication includes an emitted sound. The sound can be a specific tone, which the patient has been trained to understand that it means defibrillation is imminent. Or, the sound can be an express announcement.

The wearable defibrillator system may also optionally include a monitoring device 180, which can also be called an outside monitoring device. Monitoring device 180 is configured to monitor at least one local parameter. A local parameter can be a parameter of patient 82, or a parameter of the wearable defibrillation system, or a parameter of the environment, as will be described later. It is also based on such parameters that the wearable defibrillator system may decide whether or not to shock the patient.

Optionally, monitoring device 180 is physically coupled to support structure 170. In addition, monitoring device 180 can be communicatively coupled with other components that are coupled to support structure 170, such as a communication module, as will be deemed necessary by a person skilled in the art in view of this disclosure. Moreover, monitoring device 180 may be independently able to become communicatively coupled with other devices and components that are not necessarily coupled to support structure 170, such as a mobile phone, wireless access point (i.e. internet), and so on.

The wearable defibrillator system may also optionally include a motion sensor 181. Sensor 181 may be coupled to support structure 170 as a standalone component, or by being part of monitoring device 180, or the later described monitoring device 280. Motion sensor 181 may be made as is known in the art.

Motion sensor 181 is intended to provide a way for patient 82 to communicate with the wearable defibrillator system. Patient 82 can cause sensor 181 to detect a motion such as tapping, flicking, wiggling or shaking sensor 181, or support structure 170 near where sensor 181 is coupled to it. Such a motion is referred to as motion or "tapping" in this document. Preferably, patient 82 has been instructed where sensor 181 is located, and which deliberate motion or tapping would succeed in causing sensor 181 to detect a motion. The detected motion can become registered in the system as an entry by patient 82. The inference as to what mechanical motion is due to intentional activity by patient 82 can be processor based, waveform based, and so on. In addition, filters can also be used to identify and disregard artifact signals from motion sensor 181 that are not due to intentional tapping by patient 82.

In some embodiments, where an alarming human-perceptible indication is emitted to warn that the charge will be delivered imminently, patient 82 has the opportunity to tap support structure 170 near motion sensor 181. Sensor 181 will detect a motion, which will notify the wearable defibrillation system that patient 82 is conscious, and should not be administered a shock. In that case, the charge delivery is canceled, which means that the charge will not delivered as planned. The cancellation may take place without necessarily needing anyone to do anything else. After the cancellation, it would require a new detection of the patient signals for there to be another, subsequent intention for the charge to be delivered.

In preferred embodiments, patient 82 is only given a fixed amount of time to tap support structure 170 near motion sensor 181. This amount of time is also called a react interval, and it starts when the alarming human-perceptible indication is emitted.

In some of those embodiments, output device 171 may further emit a count-down human-perceptible indication. This indication may be in any way so as to communicate a duration of the react interval, and it may be by merely announcing how much time is left, providing an explicit count-down, intensity of indication, and so on.

Figure 2:
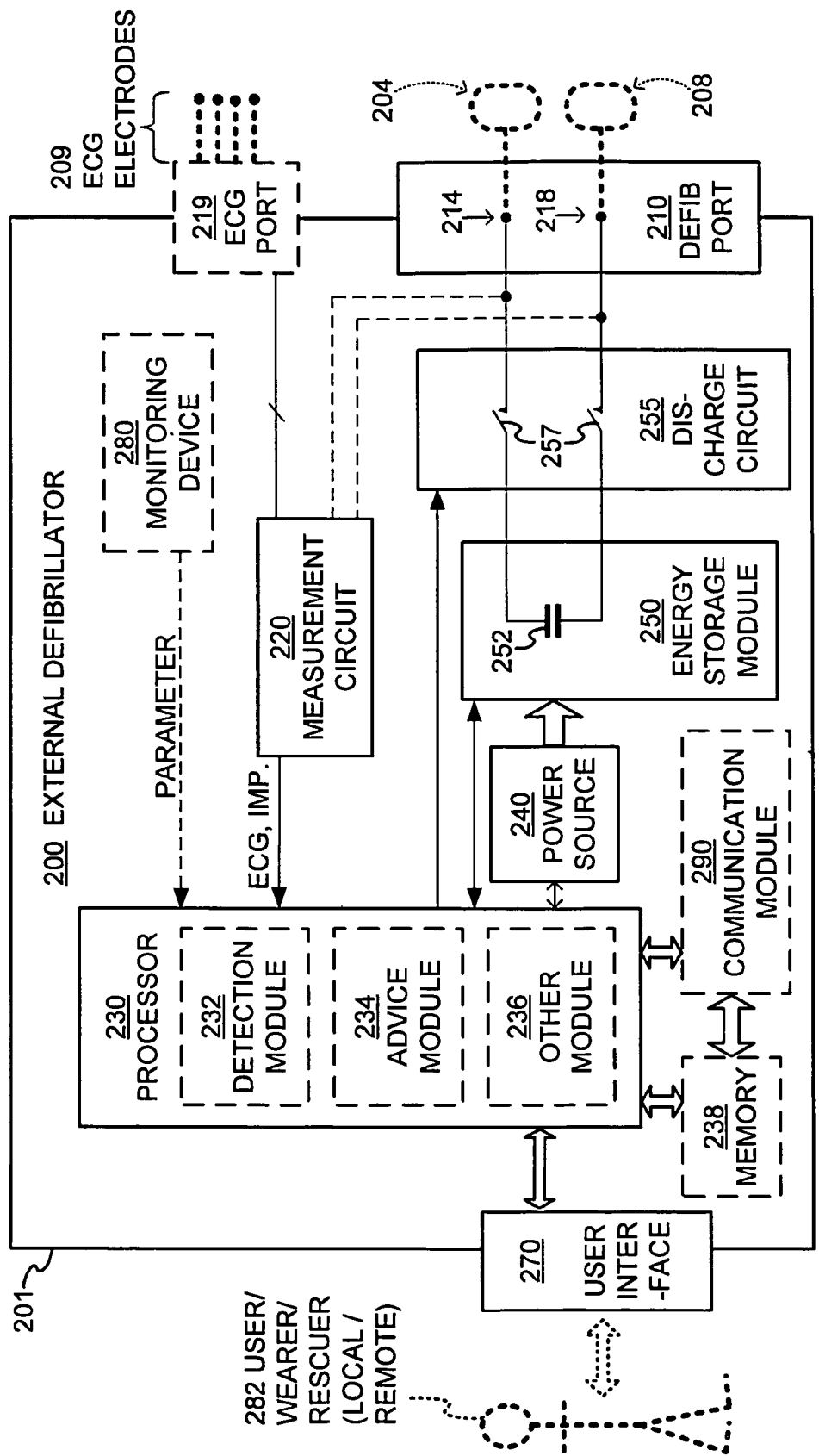
FIG. 2 is a diagram showing components of an external defibrillator, such as the one shown in FIG. 1, and which is made according to embodiments.

FIG. 2 is a diagram showing components of an external defibrillator 200, made according to embodiments. These components can be, for example, in external defibrillator 100 of FIG. 1. The components shown in FIG. 2 can be provided in a housing 201, which is also known as casing 201.

External defibrillator 200 is intended for a patient who would be wearing it, such as person 82 of FIG. 1. Defibrillator 200 may further include a user interface 270 for a user 282. User 282 can be patient 82, also known as wearer 82, if conscious. Or user 282 can be a local rescuer at the scene, such as a bystander who might offer assistance, or a trained person. Or, user 282 might be in remote communication with a remote rescuer, such as a trained person. Optionally, the user interface can be implemented instead as a smartphone or small computer that is communicatively coupled with defibrillator 200, and so on. It will be appreciated however, that user interface 270 may perform fewer functions for input, because some input functions will be performed by deliberate tapping of motion sensor 181, as described later in this document.

Defibrillator 200 may include a monitoring device 280, which can also be called an internal monitoring device because it is incorporated within housing 201. Monitoring device 280 can monitor patient parameters, system parameters and/or environmental parameters. In other words, internal monitoring device 280 can be the same, or complementary to outside monitoring device 180 of FIG. 1, and can be provided in addition to it, or instead of it. Allocating which of the system parameters are to be monitored by which monitoring device can be done according to design considerations.

Patient physiological parameters include, for example, those physiological parameters that can be of any help in detecting by the wearable defibrillation system whether the patient is in need of a shock, plus optionally their history. Example such parameters include the patient's ECG, blood oxygen level, blood flow, blood pressure, blood perfusion, pulsatile change in light transmission or reflection properties of perfused tissue, heart sounds, breathing sounds and pulse. Accordingly, appropriate monitoring devices could be a pulse oximeter, a Doppler device for detecting blood flow, a cuff for detecting blood pressure, illumination detectors and maybe sources for detecting color change in tissue, a device that can detect artery wall movement, a device with a microphone, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (ejection fraction), b) heart rate variability at rest or during exercise, c) heart rate profile during exercise and measurement of activity vigor, such as from the profile of an accelerometer signal and informed from adaptive rate pacemaker technology, d) heart rate trending, e) perfusion, such as from SpO2, CO2, f) respiratory function, respiratory rate, etc., g) motion, level of activity, and so on. Once a trend is detected, it can be stored and/or reported via a communication link, along perhaps with a warning. From the report, a physician monitoring the progress of patient 82 will know about a condition that is not improving or deteriorating.

Patient state parameters include recorded aspects of patient 82 such as motion, posture, whether they have spoken recently plus maybe also what they said, and so on, plus optionally the history of these parameters. Monitoring device 180 or monitoring device 280 may include a motion detector, which can be made in many ways as is known in the art. Or, one of these monitoring devices could include a location sensor such as GPS, which informs of the location, and the rate of change of location over time. Many motion detectors output a motion signal that is indicative of the motion of the detector, and thus of the patient's body. Patient state parameters can be very helpful in narrowing down the determination of whether SCA is indeed taking place. For example, it is known how to infer the activities and likely severity of the patient condition by interpreting motion signals. For instance, if the patient stops moving at a time when they are expected to be moving or continue moving, or exhibits other behavior that indicates that SCA may be taking place, that can be cause for increased scrutiny, and initiative to contact the patient and/or a remote doctor or caregiver.

In some embodiments, patient data of patient 82 is monitored. The patient data includes both the physiological parameters and state parameters of patient 82. The value of the physiological parameter becomes better informed from the motion profile, as is the appropriate threshold for determining whether an actionable episode is taking place. The threshold can be adjusted accordingly. For example, if the person is running, then a somewhat higher pulse rate may be tolerated until a time after they stop, and so on.

System parameters of a wearable defibrillation system can include system identification, battery status, system date and time, reports of self-testing, records of data entered, records of episodes and intervention, and so on.

Environmental parameters can include ambient temperature and pressure. A humidity sensor may provide information as to whether it is raining. Presumed patient location could also be considered an environmental parameter. The patient location could be presumed if monitoring device 180 or 280 includes a Global Positioning System (GPS) sensor.

Defibrillator 200 typically includes a defibrillation port 210, such as a socket in housing 201. Defibrillation port 210 includes nodes 214, 218. Defibrillation electrodes 204, 208, for example similar to electrodes 104, 108 of FIG. 1, can be plugged in defibrillation port 210. Plugging can be from their leads, such as leads 105 of FIG. 1, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250.

Defibrillator 200 may optionally also have an ECG port 219 in housing 201, for plugging in ECG electrodes 209, which are also known as ECG leads. It is also possible that ECG electrodes 209 can be connected continuously to ECG port 219, instead. ECG electrodes 209 can help sense an ECG signal, e.g. a 12-lead signal, or a signal from a different number of leads, especially if they make good electrical contact with the body of the patient. ECG electrodes 209 can be attached to the inside of support structure 170 for making good electrical contact with the patient, similarly as defibrillation electrodes 204, 208.

Defibrillator 200 also includes a measurement circuit 220. Measurement circuit 220 receives physiological signals from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, a person's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or ECG electrodes 209 are not making good electrical contact with the patient's body. These physiological signals can be sensed, and information about them can be rendered by circuit 220 as data, or other signals, etc.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232. Processor 230, running detection module 232, is a sample embodiment of a logic device configured to determine whether a monitored parameter has reached a specific threshold. For example, the monitoring parameter can be input from monitoring device 280, if provided. For another example, detection module 232 can include a ventricular fibrillation ("VF") detector. The patient's sensed ECG from measurement circuit 220 can be used by the VF detector to determine whether the patient is experiencing VF. Detecting VF is useful, because VF is a precursor to SCA.

Another such module in processor 230 can be an advice module 234, which generates advice for what to do. The advice can be based on outputs of detection module 232. There can be many types of advice according to embodiments. As one example, a Shock Advisory Algorithm can render the advice to shock the patient by delivering a charge, as opposed to not shock the patient. Such can be, for example, when the patient's condition has reached or exceeded an advised defibrillation threshold. Shocking can be for defibrillation, pacing, and so on.

If the advice is to shock, some external defibrillator embodiments proceed with shocking, or may advise a remote attendant to do it, and so on. As another example, the advice can be to administer CPR, and defibrillator 200 may further issue prompts for it, and so on.

Processor 230 can include additional modules, such as other module 236, for other functions. In addition, if monitoring device 280 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, nonvolatile memories (NVM), read-only memories (ROM), random access memories (RAM), any combination of these, and so on. Memory 238, if provided, can include programs for processor 230, and so on. The programs can be operational for the inherent needs of processor 230, and can also include protocols and ways that decisions can be made by advice module 234. In addition, memory 238 can store prompts for user 282, if they are a local rescuer. Moreover, memory 238 can store data. The data can include patient data, system data and environmental data, for example as learned by monitoring device 280 and monitoring device 180. The data can be stored in memory 238 before it is transmitted out of defibrillator 200, or stored there after it is received by it.

Defibrillator 200 may also include a power source 240. To enable portability of defibrillator 200, power source 240 typically includes a battery. Such a battery is typically implemented as a battery pack, which can be rechargeable or not. Sometimes, a combination is used, of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the wearable system. Module 250 is where some electrical energy is stored, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the charge for delivering to the patient.

Defibrillator 200 moreover includes a discharge circuit 255. Circuit 255 can be controlled to permit the energy stored in module 250 to be discharged to nodes 214, 218, and thus also to defibrillation electrodes 204, 208. Circuit 255 can include one or more switches 257. Those can be made in a number of ways, such as by an H-bridge, and so on.

User interface 270 can be made in any number of ways. For example, interface 270 may include a screen, to display what is detected and measured, provide visual feedback to rescuer 282 for their resuscitation attempts, and so on. Interface 270 may also include a speaker, to issue voice prompts, etc. Sounds, images, vibrations, and anything that can be perceived by user 282 can also be called human perceptible indications. Interface 270 may additionally include various controls, such as pushbuttons, keyboards, touchscreens, a microphone, and so on. In addition, discharge circuit 255 can be controlled by processor 230, or directly by user 282 via user interface 270, and so on.

Defibrillator 200 can optionally include a communication module 290, for establishing one or more wireless communication links. Module 290 may also include an antenna, portions of a processor, and other sub-components as may be deemed necessary by a person skilled in the art. This way, data and commands can be communicated, such as patient data, episode information, therapy attempted, CPR performance, system data, environmental data, and so on. Optionally, module 290 can establish at least one wired communication link, such as via a USB cable, and so on.

Defibrillator 200 can optionally include other components.

The above-mentioned devices and/or systems perform functions, processes and/or methods, as described in this document. The functions, processes and/or methods may be implemented by one or more devices that include logic circuitry. Such a device can be alternately called a computer, a device, and so on. It may be a standalone device or computer, such as a general purpose computer, or part of a device that has one or more additional functions. The logic circuitry may include a processor that may be programmable for a general purpose, or dedicated, such as microcontroller, a microprocessor, a Digital Signal Processor (DSP), and so on, or processor 230.

The logic circuitry may also include storage media, for example memory 238. Such a storage medium can be a non-transitory computer-readable medium. These storage media, individually or in combination with others, can have stored thereon programs that the processor may be able to read, and execute. More particularly, the programs can include instructions in the form of code, which the processor may be able to execute upon reading. Executing is performed by physical manipulations of physical quantities, and may result in the functions, processes and/or methods to be performed. In addition, these storage media may store data.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description also includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Figure 3A:
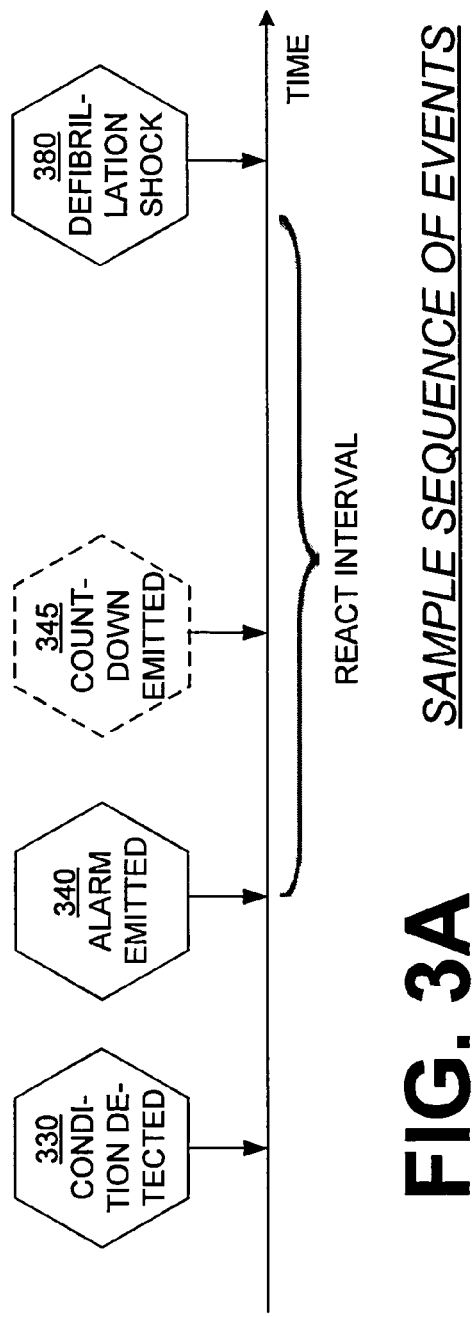
FIGS. 3A and 3B are diagrams showing sample sequences of events according to embodiments.
Figure 3B:
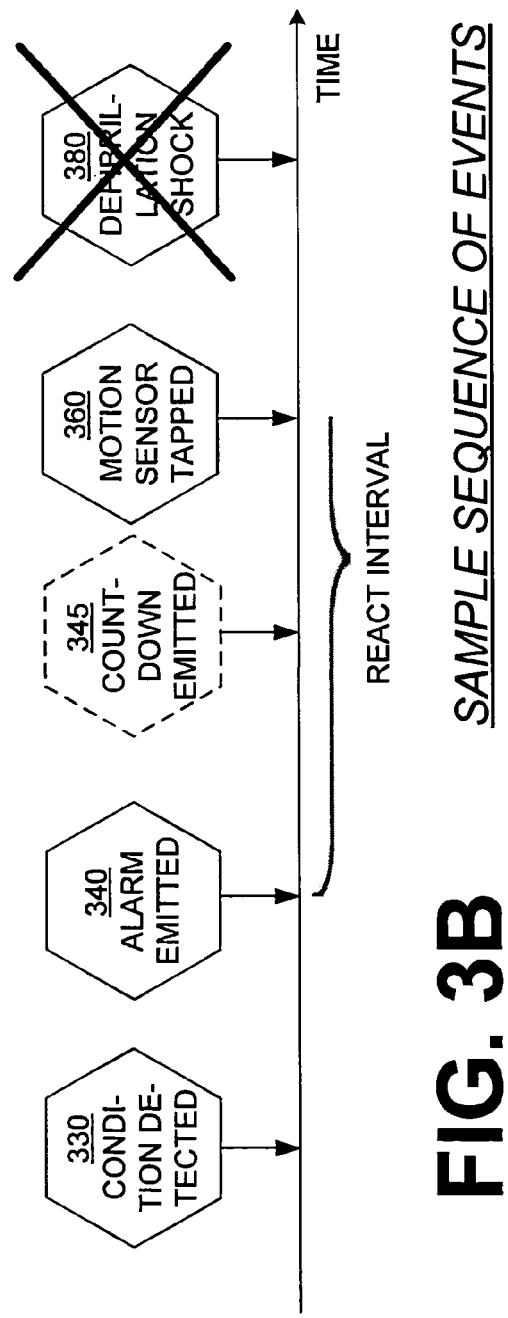

FIGS. 3A and 3B are diagrams showing sample sequences of events according to embodiments, each along a time axis. In FIG. 3A, according to event 330, a condition is detected about patient 82. The condition could be such that the patient needs to be shocked, from all of what the system was able to determine.

According to next event 340, an alarm is emitted. The alarm can be the above-mentioned alarming human-perceptible indication by output device 171, which is made when there is intent to administer a defibrillation shock imminently.

In some embodiments, event 340 also starts a react interval. According to an optional embodiment, the duration of the react interval is additionally communicated. For example, according to optional event 345, a count-down is emitted. The count-down can be a human-perceptible indication, such as an audible announcement, and so on. If the react interval passes, then according to an event 380 a defibrillation shock is administered, by having charge be delivered to the patient through electrodes.

FIG. 3B shows some of the same events as FIG. 3A. Differently, during the react interval, according to an event 360, the motion sensor is tapped. Tapping has been presumably from patient 82, and a motion has been detected from the tapping. When event 360 takes place, event 380 does not take place at the time that it would have, which it did in FIG. 3A. In other words, the administration 380 of the defibrillation shock has been canceled, as the charge delivery has been canceled. The availability of tapping so as to cause event 360 is a safeguard, for the rare case that the system improperly determined that the shock was needed. The error is proved by the fact that patient 82 tapped the system, which meant he was conscious and therefore not in need of a shock. The safeguard prevents a shock according to event 380, a shock that would have been very uncomfortable for patient 82 if he were conscious. As another observation, since event 360 took place, the react interval is not defined beyond the time of event 360.

FIG. 4 shows a flowchart 400 for describing methods according to embodiments. The methods of flowchart 400 may also be practiced by system embodiments described above.

According to an operation 440, an alarming human-perceptible indication is emitted. The alarming indication can signify that administration of a defibrillation shock is imminent, as mentioned above. Operation 440 could be event 340. Emitting the alarming indication can optionally start a react interval, as in FIG. 3A.

According to another, optional operation 445, a count-down human-perceptible indication is emitted, which communicates a duration of the react interval, as per the above. Operation 445 could be event 345, as described above.

According to another, optional operation 450, it is inquired whether the react interval has passed. If not, then according to another, optional operation 460, it is inquired whether a motion has been detected. If yes, then that is similar to event 360 of FIG. 3B and then, according to a next operation 470, the administration of the defibrillation shock is canceled. If, at operation 460 no motion is detected, execution returns to operation 445, and then to operation 450.

If, at operation 450, the react interval has passed and no motion has been detected at operation 460, then according to another operation 480, the defibrillation shock is administered to the patient imminently, such as in operation 380 of FIG. 3A.

FIG. 5 shows a flowchart 500 for describing methods according to embodiments. The methods of flowchart 500 may be practiced by patient 82, using embodiments described above.

According to an operation 510, a patient may wear a support structure of a wearable defibrillator system that includes a motion sensor. For example, the patient may wear support structure 170 an motion sensor 181. In addition, the patient may wear one or more further garments, in a manner that the one or more further garments completely cover the support structure and the motion sensor.

According to another operation 540, the patient may perceive an alarming indication that the wearable defibrillator system will administer a shock imminently. The indication may be spoken outright, or it may be a sound that the patient has been instructed means that the shock will be administered imminently. The indication may be emitted by operation 440 of FIG. 4, which may have started a react interval.

According to another operation 545, the patient may perceive a count-down indication, such as could have been emitted by operation 445. Such an operation could communicate a duration of the react interval, and let patient 82 know how much time he or she has to react by tapping support structure 170.

A decision box 550 shows how time passes during the react interval. Before the react interval has passed, operation 545 may be repeated. In addition, according to another, optional operation 560, the patient taps support structure 170. This tapping is akin to event 360 of FIG. 3B, which is detected as a motion at operation 460 of FIG. 4. If operation 560 happens then, according to another operation 570, the shock may not be received imminently, and the react interval is ended. If, however, the react interval passes then, according to another, optional operation 580, the shock is received imminently, i.e. as planned.

FIG. 6A is a diagram showing a sample sequence of events according to embodiments. The human perceptible indications are emitted by a speaker, as voice. It will be recognized that this sequence is like the sequence of FIG. 3A, except with additionally registering an inadvertent tap.

FIG. 6B is a diagram showing a sample sequence of events according to embodiments. The human perceptible indications are emitted by a speaker, as voice. It will be recognized that this sequence is like the sequence of FIG. 3B, along with a confirmation step, such as is described below.

FIGS. 7A and 7B are diagrams showing sample sequences of events according to additional embodiments, each with respect to a time axis. These embodiments are for the patient to use tapping to communicate with the device for additional purposes than described above.

In FIG. 7A, according to an event 735, a query is input. In many embodiments, a processor of the wearable defibrillation system, such as processor 230, is capable of inputting the query, which is intended to be answered for the system by the patient, as will be seen later in this document.

Inputting the query may arise in a number of ways. In some embodiments, an unscheduled motion may be detected, and the query is input responsive to the unscheduled motion. The unscheduled motion may be, for example, if patient 82 wants to engage the system. A motion is unscheduled if it does not appear to be in response to a human-perceptible indication by the system that conveys a query. Because motions may happen at random, preferably the query is input responsive to a number of unscheduled motions that follow a pattern, such as three in a short burst and with similar intervals between successive tappings. In some embodiments, patient data is monitored, and the query is input responsive to a value of the patient data exceeding a threshold. The value, for example may be cause for concern; in such cases, the system may want to act, first by asking whether the patient is feeling well.

After inputting the query, according to an event 740, the processor may cause the output device to emit a questioning human-perceptible indication, such as a sound or vibration, and which conveys the query. After having caused the query to be expressed, the answer will be expected in terms of detected motions, which will be generated by patient 82 tapping support structure 170. In some embodiments, the output device includes a vibration mechanism, and the questioning human-perceptible indication conveys the query as a vibrations pattern. For example, the query could have a first meaning if the pattern of vibrations is a first pattern, and a second, different meaning if the pattern of vibrations is a second, different pattern. The patterns could be different types of vibrations, such as continuous versus pulsating versus increasing/decreasing in intensity or amplitudes, versus different amplitudes, sequences, and so on. The patterns could also encode different messages within a type, for example like Morse code, or numbers of vibrations.

Preferably, the answer will arrive within a preset time interval, which can be called a respond interval. The respond interval can start at the time of event 740, namely when the questioning human-perceptible indication is caused to be emitted. So, in some embodiments, if no detection signal is received within the respond interval, the processor causes the output device to emit another human-perceptible indication, such as event 741. The other human-perceptible indication may be the same as the first, or different.

FIG. 7B shows some of the same events as FIG. 7A. Differently, according to an event 760, the motion sensor is tapped during the respond interval. Tapping has been presumably by patient 82, and a motion has been detected from the tapping. Tapping may be the answer expected by patient 82. Event 760 may interrupt the respond interval, similarly with how event 360 interrupts the react interval in FIG. 3B.

In such embodiments, the wearable defibrillator system may also include a component that will perform an action, as per event 790. The action will be responsive to the motions detected per event 760, after the questioning human-perceptible indication is emitted per event 740. However, in some embodiments, the action is performed only if the detection signal is received within the respond interval, and not otherwise.

There are many possible embodiments for the component and the action. For example, the component can be a communication module such as communication module 290. In such cases, the action can include transmitting a communication to a third party, such as would happen in an emergency. The third party would not be the patient, but could be a person located remotely. For another example, the component can include a memory, such as memory 238. In such cases, the action can include storing patient data in the memory, such as would happen if the patient wanted data to be captured if he were feeling ill. Or, the action could include storing in the memory a reply to the query, with the reply being in accordance with the detected motion. This could happen, for example, when the system permits patient 82 to set parameters. One example is that the query could be: "on a scale of 1-5, 5 being the best, how do you feel now?", and the number of motions, caused by the number of tappings, would indicate the reply. In other words, the reply can have a first value if the detected motion is inferred to have been caused by a first number of tappings by the patient, and a different, second value if the detected motion is inferred to have been caused by a different, second number of tappings. In addition, the query itself can be stored in memory 238.

Patient 82 may become uncertain as to how many of their tappings actually became registered, and that can be a problem where the number matters. The uncertainty can be addressed in at least two ways where patient 82 receives feedback.

First, in some embodiments, the device can emit an echo for each tapping that it registers. An echo can be a sound, a vibration, or other human-perceptible indication. An echo human-perceptible indication can be caused to be emitted for each detected motion that is interpreted to have been caused by each tapping. Emitting can be by the output device, or another device.

Second, before event 790, in some embodiments a confirmation is first asked for when patient 82 is presumed to have stopped tapping—perhaps after a long enough pause. According to an event 770, a confirming human-perceptible indication is caused to be emitted. Typically, this kind of indication conveys a proposed interpreted reply, and asks for one or two tappings for confirming or rejecting the proposed interpreted reply. In such cases, the action of event 790 can be performed only if the motion sensor is tapped again, such as per event 761, in which case another detection signal is received from the motion sensor.

FIG. 8 shows a flowchart 800 for describing methods according to embodiments. The methods of flowchart 800 may also be practiced by a processor of a wearable defibrillator system that is worn by a patient, and has a motion sensor and an output device, such as described above.

According to an optional operation 815, there is monitoring for whether an unscheduled motion is detected, or multiple motions following a pattern. While not, execution returns to operation 815. If yes, then according to another operation 835, a query is input, similarly with event 735.

According to another, optional operation 820, patient data is monitored. According to another operation 830, it is inquired whether a value of the monitored patient data exceeds a threshold. While not, execution returns to operation 820. If yes, then again operation proceeds to operation 835.

After operation 835, according to another operation 840, the output device is caused to emit a questioning human-perceptible indication that conveys the query, similarly with event 740.

According to another operation 860, a detection signal is received from the motion sensor. The detection signal may be interpreted to indicate that the patient has tapped the system, as would correspond to event 760. According to another, optional operation 865, an echo human-perceptible indication is further caused to be emitted, as above. The echo indications provide feedback to the patient.

According to another, optional operation 850, it is inquired whether the detection signal is received within a respond interval. The respond interval would start when the indication is caused to be emitted, such as from event 740. If not, execution may return to operation 840, or the output device may be caused to emit a different human-perceptible indication, and so on.

If yes, then according to another operation 890, an action is caused to be performed, responsive to the detection signal. The action being performed would be akin per event 790. Again, there are many possibilities for actions, such as causing a communication module to transmit a communication to a third party, and storing data in a memory. The data could be patient data, a reply to the query perhaps as inferred from the inferred number of tappings, and so on.

According to another, optional operation, a confirming human-perceptible indication is caused to be emitted. The confirming indication may convey a proposed interpreted reply, as per the above. In such embodiments, the action can be performed only if another detection signal is then received from the motion sensor, which would serve as a confirmation by the patient.

Figure 9:
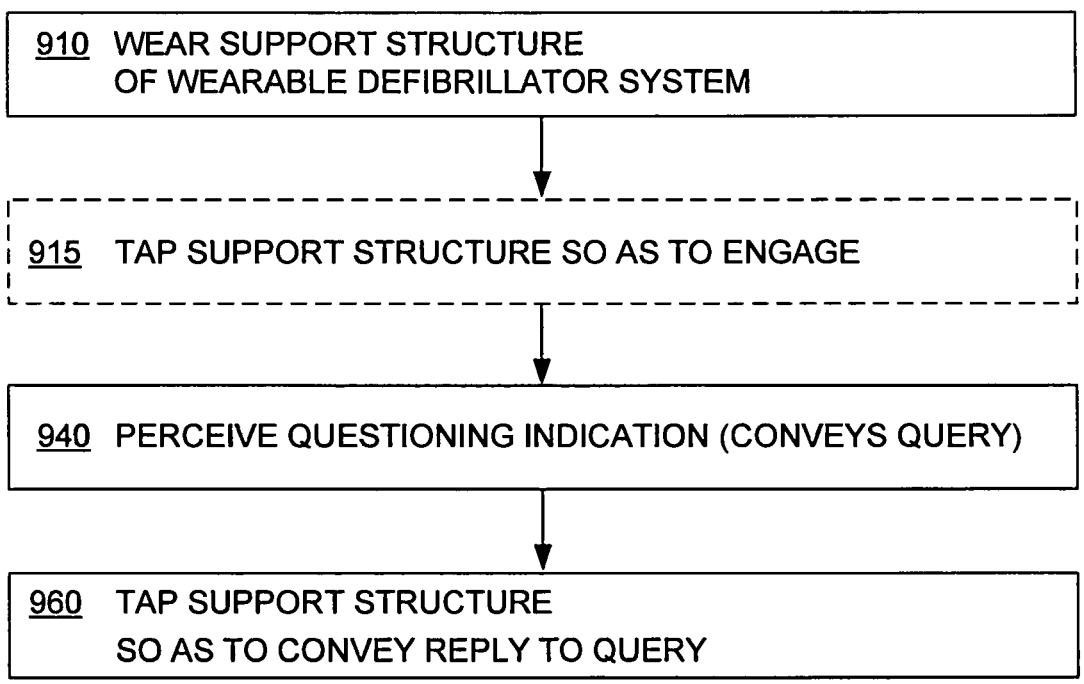
FIG. 9 is a flowchart for illustrating methods according to additional embodiments.

FIG. 9 shows a flowchart 900 for describing methods according to embodiments. The methods of flowchart 900 may be practiced by patient 82, using embodiments described above.

According to an operation 910, a patient may wear a support structure of a wearable defibrillator system, such as support structure 170. The system may include a motion sensor.

According to another, optional operation 915, the patient may preliminarily tap proximately to the support structure, so as to draw the attention of the system. Tapping proximately to the support structure tapping means on the structure or close to it, so as to cause the motion sensor to move, and thus detect a motion and generate a detection signal. This preliminary tapping will be unscheduled, from the point of view of the system, and may result in an unscheduled motion being detected as per operation 815. The tapping of operation 915 can be in a pattern designed to engage the system, and so on.

According to another operation 940, the patient may perceive a questioning indication that conveys a query from the system. Operation 940 may be event 740 of FIG. 7. The questioning indication of operation 940 maybe spoken outright, or it may be a sound, a vibration and so on. The questioning indication may be emitted by operation 840 of FIG. 8, which may have started a respond interval.

According to another, optional operation 960, the patient taps support structure 170. This tapping is akin to event 760 of FIG. 7B, and is intended to convey a reply in response to the query. In some embodiments, the number of tappings is meaningful. For example, a first number of tappings may convey a reply with a first value, and a second, different number of tappings may convey a reply with a second, different value.

According to another, optional operation, a confirming indication is perceived by the patient from the system. The confirming indication may convey a proposed interpreted reply, as per the above. In such embodiments, the patient may tap again the support structure in response to the confirming indication.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

FIG. 10 is a diagram showing a sample sequence of events according to additional embodiments. The human perceptible indications are emitted by a speaker, as voice.

This description includes one or more examples, but that does not limit how the invention may be practiced. Indeed, examples or embodiments of the invention may be practiced according to what is described, or yet differently, and also in conjunction with other present or future technologies.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment, extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and sub-combinations of elements, features and steps or operations, which are regarded as novel and non-obvious. Additional claims for other such combinations and subcombinations may be presented in this or a related document.

What is claimed is:

1. A wearable defibrillator system, comprising:
a support structure for wearing by a patient:
electrodes for delivering a charge to the patient, while the patient is wearing the support structure;
an output device;
a processor for inputting a query, and for causing the output device to emit a questioning human-perceptible indication that conveys the query;
a motion sensor configured to detect motion of the patient while the patient responds to the query; and
a communication module for transmitting a communication to a third party responsive to a motion detected by the motion sensor after the questioning human-perceptible indication is emitted.

2. The system of claim 1, in which
the output device includes a speaker.

3. The system of claim 1, in which
the output device includes a vibration mechanism.

4. The system of claim 1, in which
an unscheduled motion is detected, and
the query is input responsive to the unscheduled motion.

5. The system of claim 4, in which
a plurality of unscheduled motions following a pattern are detected, and
the query is input responsive to the plurality of unscheduled motions.

6. The system of claim 1, further comprising:
a monitoring device for monitoring patient data, and
in which the query is input responsive to a value of the patient data exceeding a threshold.

7. The system of claim 1, in which
the output device includes a vibration mechanism, and
the questioning human-perceptible indication conveys the query as a pattern of vibrations, such that
the query has a first meaning if the pattern of vibrations is a first pattern, and
the query has a second meaning different from the first meaning if the pattern of vibrations is a second pattern different from the first pattern.

8. The system of claim 1, in which
the communication to the third party is transmitted only if the motion is detected within a respond interval that starts when the questioning human-perceptible indication is caused to be emitted, and
if no motion is detected within the respond interval, the processor causes the output device to emit another human-perceptible indication.

9. The system of claim 1, in which
an echo human-perceptible indication is further caused to be emitted for each detected motion that is interpreted to have been caused by each tapping.

10. The system of claim 1, in which
a confirming human-perceptible indication is caused to be emitted, and
the communication to the third party is transmitted only if another motion signal is then received from the motion sensor.

11. A non-transitory computer-readable storage medium storing one or more programs which, when executed by a processor of a wearable defibrillator system that is worn by a patient, and has a motion sensor, an output device, and a communication module, they result in:
  inputting a query;
  causing the output device to emit a questioning human-perceptible indication that conveys the query;
  then receiving a detection signal from the motion sensor wherein the motion sensor is configured to detect motion of the patient while the patient responds to the query; and
  causing a communication to be transmitted to a third party responsive to the detection signal.

12. The medium of claim 11, in which
  an unscheduled detection signal is received, and
  the query is input responsive to the unscheduled detection signal.

13. The medium of claim 12, in which
  a plurality of unscheduled detection signals following a pattern are received, and
  the query is input responsive to the plurality of unscheduled detection signals.

14. The medium of claim 11, in which
  the wearable defibrillator system further has a monitoring device for monitoring patient data, and
  in which the query is input responsive to a value of the patient data exceeding a threshold.

15. The medium of claim 11, in which
  the output device includes a vibration mechanism, and
  the questioning human-perceptible indication conveys the query as a pattern of vibrations, such that:
  the query has a first meaning if the pattern of vibrations is a first pattern, and
  the query has a second meaning different from the first meaning if the pattern of vibrations is a second pattern different from the first pattern.

16. The medium of claim 11, in which
  an echo human-perceptible indication is further caused to be emitted for each detection signal that is interpreted to have been caused by each tapping.

17. The medium of claim 11, in which
  the communication to the third party is caused to be transmitted only if the detection signal is received within a respond interval that starts when the questioning human-perceptible indication is caused to be emitted, and
  if no detection signal is received within the respond interval, the output device is caused to emit another human-perceptible indication.

18. The medium of claim 11, in which executing the one or more programs further results in:
  causing to be emitted a confirming human-perceptible indication, and
  in which the communication to the third party is transmitted only if another detection signal is then received from the motion sensor.

19. A wearable defibrillator system, comprising:
  a support structure for wearing by a patient;
  electrodes for delivering a charge to the patient, while the patient is wearing the support structure;
  an output device;
  a processor for inputting a query, and for causing the output device to emit a questioning human-perceptible indication that conveys the query;
  a monitoring device for monitoring patient data; and
  a motion sensor configured to detect motion of the patient while the patient responds to the query; and
  a memory for storing the patient data responsive to a motion detected by the motion sensor after the questioning human-perceptible indication is emitted.

20. A non-transitory computer-readable storage medium storing one or more programs which, when executed by a processor of a wearable defibrillator system that is worn by a patient, and has a motion sensor, an output device, a memory, and a monitoring device, they result in:
  monitoring patient data;
  inputting a query;
  causing the output device to emit a questioning human-perceptible indication that conveys the query;
  then receiving a detection signal from the motion sensor wherein the motion sensor is configured to detect motion of the patient while the patient responds to the query; and
  causing the patient data to be stored in the memory responsive to the detection signal.

21. A wearable defibrillator system, comprising:
  a support structure for wearing by a patient;
  electrodes for delivering a charge to the patient, while the patient is wearing the support structure;
  an output device;
  a processor for inputting a query, and for causing the output device to emit a questioning human-perceptible indication that conveys the query;
  a motion sensor configured to detect motion of the patient while the patient responds to the query; and
  a memory for storing a reply to the query responsive to a motion detected by the motion sensor after the questioning human-perceptible indication is emitted, the reply in accordance with the detected motion.

22. A non-transitory computer-readable storage medium storing one or more programs which, when executed by a processor of a wearable defibrillator system that is worn by a patient, and has a motion sensor, an output device and a memory, they result in:
  inputting a query;
  causing the output device to emit a questioning human-perceptible indication that conveys the query;
  then receiving a detection signal from the motion sensor wherein the motion sensor is configured to detect motion of the patient while the patient responds to the query; and
  causing a reply to the query to be stored in the memory responsive to the detection signal, the reply in accordance with the detection signal.

23. A method comprising:
  wearing a support structure of a wearable defibrillator system that includes a motion sensor, wherein the motion sensor is configured to detect motion of the patient while the patient responds to the query;
  perceiving a questioning indication that conveys a query; and
  tapping deliberately proximately to the support structure so as to cause the motion sensor to move in order to convey a reply in response to the query, in which a first number of tappings conveys that the reply has a first value, and a second number of tappings different from the first number conveys that the reply has a second value different from the first value.

24. The method of claim 23, further comprising:
  tapping proximately to the support structure prior to perceiving the questioning indication, and
  in which the questioning indication is perceived in response to preliminarily tapping.

25. The method of claim 23, further comprising:
  perceiving a confirming indication; and tapping again proximately to the support structure in response to the confirming indication.

26. The method of claim 23, further comprising:
wearing one or more further garments in a manner that the one or more further garments completely cover the support structure and the motion sensor.

\* \* \* \* \*